United States Patent [19]

Trombone

[11] Patent Number: 4,469,627
[45] Date of Patent: Sep. 4, 1984

[54] PROCESS FOR DISPERSING HYDROXYPROPYL METHYL CELLULOSE

[75] Inventor: Thomas J. Trombone, Brooklyn, N.Y.

[73] Assignee: Colgate-Palmolive Company, New York, N.Y.

[21] Appl. No.: 414,688

[22] Filed: Sep. 3, 1982

[51] Int. Cl.$^3$ .......................... C11D 1/14; C08L 1/08
[52] U.S. Cl. .................................. 252/548; 106/170; 106/171; 106/177; 106/178; 106/186; 106/197 R; 424/70; 252/174.11; 252/174.16; 252/174.17; 252/DIG. 13
[58] Field of Search ............... 106/171, 177, 178, 197, 106/170, 199, 180, 186; 536/87; 252/174.16, 174.11, 174.17, 548, DIG. 13

[56] References Cited

U.S. PATENT DOCUMENTS

| | | | |
|---|---|---|---|
| 3,402,137 | 9/1968 | Fisher et al. | 524/321 |
| 3,503,895 | 3/1970 | Whelan | 252/363.5 |
| 3,522,070 | 7/1970 | Webb | 106/170 |
| 3,960,584 | 6/1976 | Savage | 106/197 R |
| 4,231,802 | 11/1980 | McGinley | 106/199 |
| 4,330,414 | 5/1982 | Hoover | 106/189 |
| 4,414,144 | 11/1983 | Liebowitz | 252/174.17 |

*Primary Examiner*—Theodore Morris
*Attorney, Agent, or Firm*—Herbert S. Sylvester; Murray M. Grill; Norman Blumenkopf

[57] ABSTRACT

A method of facilitating the incorporation of hydroxypropyl methyl cellulose (HPMC) into a liquid formulation containing water which comprises:

1. forming a liquid premix of hydroxypropyl methyl cellulose dispersed in an aqueous-free organic liquid medium in which it does not swell or dissolve, selected from the group consisting of liquified nonionic surfactants, fatty acids, anionic surfactants and mixtures thereof, by dispersing HPMC in said liquified organic medium with mild agitation;

2. adding said premix to an aqueous-containing liquid formulation and dispersing therein by means of a short mixing cycle as short as 5–10 minutes. This method has particular utility in the preparation of liquid shampoos, liquid dishwashing detergents, liquid hand soaps and other aqueous-containing liquid formulations wherein it is desirable or necessary to include hydroxypropyl methyl cellulose as a viscosity modifier.

12 Claims, No Drawings

PROCESS FOR DISPERSING HYDROXYPROPYL METHYL CELLULOSE

BACKGROUND AND PRIOR ART

The present invention relates to a process for dispersing hydroxypropyl methyl cellulose in a nonaqueous liquified organic medium in which it does not swell or dissolve, and subsequently adding said dispersion to an aqueous-containing liquid formulation wherein it is readily solubilized.

Hydroxypropyl methyl cellulose is often used as a thickening agent in aqueous-containing liquid formulations such as liquid detergents, shampoos, liquid hand soaps and the like. However, processing difficulties are encountered when dispersing and incorporating hydroxypropyl methyl cellulose into liquid formulations containing water, using conventional methods of dispersion. These known methods include dispersion in hot water at temperatures of 80°–100° C. (176°–212° F.); dispersion in water miscible organic solvents such as alcohol or glycol; and dispersion by dry blending with dry powders. The disadvantages of aforesaid conventional methods are the use of large amounts of energy in the form of heat and long mixing cycles; and the presence of flammable solvents such as alcohol which creates the danger of inflammability.

Still another difficulty encountered with aforesaid dispersion methods is the formation of lumps of undissolved hydroxypropyl methyl cellulose in the aqueous medium, which do not dissolve even after protracted periods of agitation (about 2–3 hours). This lumping problem requires an additional filtration step to rid the liquid formulation of said undissolved material. In addition, it is necessary to heat the water to high temperatures of about 75°–100° C. to effect dispersion of the hydroxypropyl methyl cellulose therein. This is shown in U.S. Pat. No. 3,953,591 wherein is disclosed the method of preparing a skin conditioning emulsion by separately heating the oil phase and the water phase containing the hydroxypropyl methyl cellulose, each to a temperature of 75°–100° C., and slowly adding the heated oil phase to the water phase with stirring (column 4 lines 21–34).

U.S. Pat. No. 3,549,542 also discloses the necessity of using hot water heated to a temperature of 180°–200° F. for dispersing the hydroxypropyl methyl cellulose in water prior to the addition of an aqueous solution of a cationic polymer to form a premix, which is subsequently dispersed in an aqueous solution of an anionic detergent, followed by milling in a colloid mill, to form a homogeneous liquid detergent composition.

U.S. Pat. No. 3,998,761 also discloses the necessity of using water heated to a temperature of about 185°–190° F. to slowly disperse hydroxypropyl methyl cellulose powder under rapid lightning agitation and the addition, with agitation, of a formaldehyde solution in the formation of a lump free mucilage. This mucilage is prepared a day prior to its addition to a shampoo formulation.

U.S. Pat. No. 4,174,305 discloses the preparation of a granular detergent composition by combining all the components except the cellulose ether (Methocel HB 15000) in an aqueous crutcher slurry, spray drying to granule form and adding the cellulose ether to the granules as a dry admix. The liquid compositions are prepared by mixing the components in a liquid carrier of water or water and alcohol.

However, there is no disclosure of the preparation of a premix of hydroxypropyl methyl cellulose dispersed in an aqueous-free liquified organic medium in which it does not swell or dissolve, selected from the group consisting of liquified nonionic surfactants, fatty acids, anionic surfactants and mixtures thereof, prior to its incorporation into an aqueous-containing liquid formulation, using a short mixing cycle.

SUMMARY OF THE INVENTION

The primary object of the invention is to provide an improved method for dispersing hydroxypropyl methyl cellulose in an aqueous-containing liquid formulation.

Another object of the invention is to provide an improved method to overcome the processing difficulties when dispersing and incorporating hydroxypropyl methyl cellulose into liquid formulations containing water.

Still another object of this invention is to provide an improved method of dispersing hydroxypropyl methyl cellulose into liquid formulations containing water, by first dispersing with mild agitation, in an aqueous-free organic medium in which it does not swell or dissolve, prior to its addition to said aqueous-containing liquid.

Still another object of this invention is to provide a method of preparing a premix of a dispersion of hydroxypropyl methyl cellulose in an aqueous-free liquified organic medium selected from the group consisting of nonionic surfactants, fatty acids, anionic surfactants and mixtures thereof.

Still another object of this invention is to provide a method of readily dispersing hydroxypropyl methyl cellulose in an aqueous-containing liquid formulation utilizing a short mixing cycle.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the method of this invention facilitates the incorporation of hydroxypropyl methyl cellulose into water or liquid formulations containing water which comprises dispersing hydroxypropyl methyl cellulose in an aqueous-free organic liquid medium in which it does not swell or dissolve, selected from the group consisting of liquified nonionic surfactants, fatty acids, anionic surfactants and mixtures thereof, to form a liquid premix. This dispersion can be maintained at a temperature sufficient enough to retain its fluidity for incorporation into said water-containing liquid formulation; or said premix dispersion can be allowed to solidify upon cooling to room temperature; and be remelted when needed. The hydroxypropyl methyl cellulose may be dispersed into said nonaqueous liquid organic medium at a ratio of 1 part hydroxypropyl methyl cellulose to about 1 to 10 parts organic medium, and preferably the formula amount of said organic dispersant ingredients.

More specifically, present invention relates to an improved method of dispersing hydroxypropyl methyl cellulose into liquid formulations containing water, which comprises:

1. liquifying, if said organic medium is not liquid at room temperature, and blending (if necessary) an aqueous-free organic medium in which hyroxypropyl methyl cellulose does not swell or dissolve, selected from the group consisting of nonionic surfactants, fatty acids, anionic surfactants and mixtures thereof, by heating to a temperature of about 75°–120° F.;

2. adding hydroxypropyl methyl cellulose to said organic liquified medium and dispersing therein with mild agitation to form a premix dispersion;

3. adding said premix dispersion to water or a water-containing formulation, and dispersing therein by means of a short mixing cycle of about 5–10 minutes, to form a homogeneous liquid. The premix dispersion of hydroxypropyl methyl cellulose (HPMC) and nonaqueous organic medium, when made in the ratio required for processing, such as in the preparation of a shampoo, can be readily added to the formula amount of water, wherein it is readily solubilized. For example, a premix of Methocel (HPMC) dispersed in a blended liquid mixture of lauric diethanolamide, lauric acid and polyoxyethylene lauryl ether phosphate liquified at 110° F., can readily be pumped into the formula amount of water in the formation of a homogeneous liquid, free of lumps. This premix, which is a paste at 77° F., can similarly be added to the formula amount of water and form a homogeneous liquid, free of lumping. Thus, it is apparent that said premix dispersion is equally effective in the form of a liquid or paste.

Hydroxypropyl methyl cellulose is a cellulosic polymer in the form of a white or off-white granular product, typically commercially available from the Dow Chemical Co. as Methocel, in the form of a fine powder. This polymer dissolves in water and in certain organic solvents by swelling and successive hydration of their structural layers. Accordingly, in order to make gel-free solutions of Methocel, it is necessary to first disperse the particles in the water or organic solvent with continuous agitation so that each particle is wetted, after which time it hydrates and builds viscosity.

It has been unexpectedly found that the premix of hydroxypropyl methyl cellulose dispersed in a nonaqueous organic medium in which it does not swell nor dissolve, can be readily mixed with water or a liquid formulation containing water, in the formation of a homogeneous liquid free of particles or lumps, using a short mixing cycle of about 5–10 minutes, as opposed to a 2 or 3 hour mixing period heretofore utilized. In a comparative test using a Methocel/urea blend, the two powders are blended for 2½ hours on rollers, prior to the addition of said blend to a mixer containing an aqueous shampoo formulation, and agitated for 2 hours. The resultant liquid shampoo still had lumps.

It has additionally been unexpectedly found that the hydroxypropyl methyl cellulose premix of this invention, which may solidify at room temperature, has the capability of being reliquified at temperatures of about 85°–105° F., and is equally effective in the preparation of a homogeneous, lump-free liquid formulation containing water, after only a short mixing cycle. Freshly made hydroxypropyl methyl cellulose premix and 24 hour-old remelted premix give identical final products.

It has additionally been found that the addition of perfume, an ingredient often found in aqueous liquid formulations such as shampoos, to the premix dispersion of nonaqueous organic liquid medium and hydroxypropyl methyl cellulose, retains the liquidity of said premix at room temperature. This is advantageous in that heat is not required to reliquify the premix which solidifies at room temperature into a pasty material. Although the liquid or paste form of said premix can be incorporated into the aqueous-containing liquid formulation, it is preferable to utilize the liquid form because of the pumping equipment generally used in the preparation of liquid formulations. The perfume ingredient, which is soluble in organic liquids, is readily blended with the nonaqueous organic medium of the premix. The hydroxypropyl methyl cellulose does settle on standing, but agitation disperses it readily. The dual advantage of including the perfume in the premix is the elimination of the use of heat to liquify the pasty unperfumed premix, and the necessity of maintaining said mix at an elevated temperature in order to pump it into the aqueous-containing liquid formulation.

In accordance with this invention, the nonionic surfactants suitable for use as a dispersing agent for the hydroxypropyl methyl cellulose must be a liquid, or capable of being liquified at low temperatures of about 75°–120° F. The nonionic synthetic organic detergents are generally the condensation product of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a nonionic detergent. A preferred nonionic surfactant herein is ethylene glycol distearate.

The nonionic detergents include the polyethylene oxide condensate of one mole of alkyl phenol containing from about 6 to 12 carbon atoms in a straight- or branched-chain configuration with about 5 to 30 moles of ethylene oxide, for example, nonyl phenol condensed with 9 moles of ethylene oxide, dodecyl phenol condensed with 15 moles of ethylene and dinonyl phenol condensed with 15 moles of ethylene oxide. Condensation products of the corresponding alkyl thiophenols with 5 to 30 moles of ethylene oxide are also suitable.

Also included in the nonionic detergent class are the condensation products of a higher alcohol (e.g. an alkanol containing about 8 to 18 carbon atoms in a straight or branched-chain configuration) condensed with about 5 to 30 moles of ethylene oxide, for example, laurylmyristy alcohol condensed with about 16 moles of ethylene oxide.

One group of nonionics is marketed under the trade name "Pluronic". The compounds are formed by condensing ethylene oxide with a hydrophobic base formed by the condensation of propylene oxide with propylene glycol.

Other suitable nonionic surfactants include polyethoxylated hexitan fatty acid esters such as polyoxyethylene (20 or 80) sorbitan monolaurate, polyoxyethylene sorbitan monostearate, polyoxyethylene sorbitan or mannitan palmitate or oleate, with the number of ethoxies varying from 15 to 80.

A preferred group of nonionic surfactant particularly useful herein are the mono- and di-ethanolamide of higher fatty acids having 10 to 18 carbon atoms, such as cocomonoethanolamide, cocodiethanolamide, lauric myristic diethanolamide, lauric monoethanolamide and lauric diethanolamide. Polyacrylamides may also be utilized.

The aliphatic amine oxides of the general formula $R_1R_2R_3N \rightarrow O$ are nonionic at a pH of 6.5 to 7.5, and may also be used herein. $R_1$ is an alkyl, alkenyl, or monohydroxyalkyl radical having about 10 to 16 carbon atoms, $R_2$ and $R_3$ are each selected from the group consisting of methyl, ethyl, propyl, ethanol, and propanol radicals. Examples of suitable amine oxides include dimethyl lauryl amine oxide, dimethyl cetyl amine oxide, dimethylmyristyl amine oxide.

Another group of suitable organic dispersants for the hydroxypropyl methyl cellulose are the higher fatty acids containing 10 to 31 carbon atoms in their chain, which can be liquified at low temperatures of about 75° to 120° F. Examples of suitable fatty acids include lauric acid, palmitic acid, stearic acid, oleic acid, lanolin fatty acids, capric acid, and undecylic acid.

Still another group of suitable organic dispersants for hydroxypropyl methyl cellulose are the anionic surfactants which are liquid at room temperature or can be liquified at low heat, temperatures of about 75° to 120° F. Examples of suitable anionic surfactants are the water soluble salts, e.g. sodium, potassium, ammonium, alkylolammonium and triethanolammonium salts of higher alkyl benzene sulfonates and phosphonates, higher alkyl toluene sulfonates and phosphonates, higher alkyl phenol sulfonates and phosphonates and higher naphthalene sulfonates and phosphonates; paraffin sulfonates and phosphonates containing about 10 to 20 carbon atoms; sodium and potassium sulfates and phosphates of higher alcohols containing 8 to 18 carbon atoms such as sodium lauryl sulfate or phosphate and sodium tallow alcohol sulfate or phosphate, sodium and potassium salts of a-sulfofatty or phosphofatty acid esters containing about 10 to 20 carbon atoms in the acyl group, for example, methyl a-sulfo- or phosphomyristate and methyl a-sulfotallowate, ammonium sulfates and phosphates of mono- or di-glycerides of higher ($C_{10}$–$C_{18}$) fatty acids, for example, stearic monoglyceride monosulfate or phosphate; sodium higher alkyl ($C_{10}$–$C_{18}$) glyceryl ether sulfonates and phosphonates; and sodium or potassium alkyl phenol polyethenoxy ether sulfates and phosphates with about 1 to 6 oxyethylene groups per molecule and in which the alkyl radicals contain about 8 to about 12 carbon atoms.

Other suitable anionic surface active agents include the $C_8$ to $C_{18}$ acyl sarcosinates (for example sodium lauroyl sarcosinate); sodium and potassium salts of the reaction product of higher fatty acids containing 8 to 18 carbon atoms in the molecule esterified with isethionic acid; and sodium and potassium salts of the $C_8$ to $C_{18}$ acyl N-methyl taurides, for example, sodium cocoyl methyl taurate and potassium stearoly methyl taurate.

DETAILED DESCRIPTION OF THE INVENTION

The following specific examples are further illustrative of the present invention, but is is understood that the invention is not limited thereto. All amounts of various ingredients are by weight unless otherwise specified.

EXAMPLE 1

| Pre-Mix, Blend | % |
| --- | --- |
| Lauric diethanolamide | 3.0 |
| Lauric Acid | 1.0 |
| MEP-103[1] | 0.5 |
| Methocel E4M[2] | 1.0 |

[1]Polyoxyethylene lauryl ether phosphate
[2]Hydroxypropyl methyl cellulose powder having a methoxyl content of 28-30%, a hydroxypropyl content of 7-12%, and a viscosity at 20° C. (2% solu.) of 3,500 cps-5,600 cps, supplied by Dow Chemical Company The first three ingredients are mixed together and heated to 120° F. to insure liquifaction of the lauric acid flakes, and forms a melted liquid mixture thereof. Then Methocel is added to the above liquid ingredients with mixing. The resulting premix is a thin liquid @120° F.

@110° F.—thin fluid
@100° F.—thin fluid
@90° F.—thickening but pourable
@80° F.—thickening but pourable
@70° F.—thickening but pourable
@65° F.—pasty The 87° F. premix is added to the aqueous mixture of the remaining ingredients of a typical shampoo formulation, using mild agitation. Small clumps or lumps seem to form but within 5 minutes of good agitation, the shampoo formulation is a homogeneous liquid with no particles or lumps.

EXAMPLE 2

The premix of Example 1 is allowed to cool overnight to room temperature, whereupon it solidifies into a paste. The solidified premix is completely liquified at 105° F. The remelted premix at 90° F. is added to the aqueous mixture of the other shampoo ingredients, and mixed 10 minutes with strong agitation.

The resulting shampoo formulation is a homogeneous liquid having no undissolved particles.

Both Examples 1 and 2 processed identically. There is no difference in using a freshly made or a remelted premix dispersion of hydroxypropyl methyl cellulose in an aqueous-free organic medium.

EXAMPLE 3

The premix of Example 1 is allowed to cool to 77° F. and forms a paste. This paste is added to the formula amount of water in a shampoo formulation. No lumping occurs. The aqueous mixture remains fluid. Although the paste form of the premix is not pumpable, it can be used where processing does not depend upon pumps as a means of addition to the liquid formulations.

EXAMPLES 4 and 5 Premix (in formula amount)

| Ingredient | 4 % | 5 % |
| --- | --- | --- |
| Lauric diethanolamide | 3.000 | 5.000 |
| Lauric Acid | 1.000 | 1.000 |
| MEP-103[1] | 0.500 | 0.500 |
| Methocel E4M[2] | 1.010 | 0.825 |
| Perfume | 0.800 | 0.800 |
| Viscosity @ 77° F. = | 1170 cps | 900 cps |

Procedure

The first three ingredients are heated until liquid, approximately 120° F. The Methocel is added to the liquid medium, and mixed thoroughly. The perfume is then added to the above dispersion and also mixed thoroughly. The perfume or fragrance may be added to the liquid medium, wherein it dissolves, prior to the addition of the Methocel. Both premixes remain liquid after cooling to room temperature. The Methocel does settle on standing but mild agitation disperses it readily.

These examples show that the premix containing perfume retains its liquid state at room temperature, as compared to a pasty consistency without the perfume. Although the presence of perfume in the premix is not essential, it is a preferred optional ingredient. The advantage of the perfumed premix is the elimination of the necessity of heating the premix in order to liquify the pasty unperfumed premix and to maintain it at an elevated temperature in order to pump it.

EXAMPLE 6

3 g Neodol 25-7 (ethoxylated $C_{12-15}$ alcohol containing 7 moles ethylene oxide per mole) which is a nonionic liquid at room temperature, is mixed with 0.5 g HPMC to form a nonaqueous liquid dispersion at room temperature.

This liquid premix is added to a warm (120° F.) aqueous solution containing 60 g triethanolamine lauryl sulfate and 40 g water, and mixed well for about 5 minutes. The HPMC readily dissolves in said aqueous solution and forms a homogeneous liquid free of lumps, which may be used in the laundering of fabrics.

EXAMPLE 7

3 g stearic acid, which is in the form of flakes, is liquified by heating to 120° F. 0.5 g HPMC is added to, and mixed with the liquid stearic acid to form a warm nonaqueous liquid dispersion of HPMC.

This warm liquid premix is added to an aqueous solution comprising 60 g triethanolamine lauryl sulfate and 40 g water, and mixed well for 5 minutes. The HPMC dissolves readily in said aqueous solution and forms a lump-free homogeneous liquid detergent formulation.

EXAMPLE 8

3 g ethylene glycol distearate is heated to 120° F. to liquify. 0.5 g HPMC is added to said nonaqueous liquid medium with mixing. The HPMC readily disperses therein, to form a warm premix.

This warm premix is added to an aqueous solution of 40 g water and 60 g triethanolamine lauryl sulfate and mixed 5 minutes. The HPMC readily dissolves in said aqueous medium and forms a lump-free homogeneous liquid detergent.

Other nonaqueous organic dispersing mediums may be substituted for the specific dispersants recited in the examples, provided the hydroxypropyl methyl cellulose does not swell or dissolve therein.

This novel method may be used to incorporate hydroxypropyl methyl cellulose in aqueous-containing liquid formulations, such as shampoos, liquid soaps, liquid detergents including dishwashing liquids, fabric laundering liquids and the like. The resulting products are stable, homogeneous liquids, free of lumps of hydroxypropyl methyl cellulose.

The present method is more economical, uses less energy (heat), eliminates the filtration step and avoids the use of flammable solvents such as alcohol, heretofore used. The use of perfumed and unperfumed premix has overcome the processing difficulties and facilitated the incorporation of hydroxypropyl methyl cellulose into aqueous-containing liquid formulations.

Although the present invention has been described and illustrated with reference to specific examples, it is understood that modifications and variations of composition and procedure are contemplated within the scope of the following claims.

I claim:

1. A method which facilitates the incorporation of hydroxypropyl methyl cellulose into water or liquid formulations containing water, which comprises forming a premix of hydroxypropyl methyl cellulose dispersed in an aqueous-free organic liquid medium dispersant in which it does not swell or dissolve, selected from the group consisting of liquified nonionic surfactants, higher fatty acids containing 10 to 31 carbon atoms in their chain, anionic surfactants and mixtures thereof, by dispersing one part hydroxypropyl methyl cellulose in about 1 to 10 parts of said liquid organic medium with mild agitation; adding said premix to water or an aqueous-containing liquid formulation, and dispersing therein by means of a short mixing cycle.

2. The method in accordance with claim 1, wherein said organic medium dispersant is liquified by heating at a temperature of about 75°–120° F.

3. The method in accordance with claim 2, wherein said premix dispersion is in the form of a warm liquid which is readily dispersed in water or a water-containing liquid formulation, to form a homogeneous liquid free of particles and lumps.

4. The method of claim 2, wherein said premix is allowed to cool to room temperature and solidify into a paste which is readily incorporated into water or an aqueous-containing liquid formulation to form a lump-free homogeneous liquid.

5. The method in accordance with claim 4, wherein said solidified premix is aged and then reliquified by heating to a temperature of about 85° to 105° F., prior to addition to water or a water-containing liquid formulation.

6. The method in accordance with claim 1, wherein the short mixing cycle is as short as about 5 to 10 minutes.

7. The method in accordance with claim 1, wherein a perfume is added to said premix to form a perfumed premix which retains its liquid state upon cooling to room temperature.

8. The method in accordance with claim 1, wherein the water-containing liquid formulation is a shampoo, and the premix constitutes said formula amount of hydroxypropyl methyl cellulose and aqueous-free organic dispersant ingredients.

9. The method in accordance with claim 1, wherein the nonaqueous organic dispersant for the hydroxypropyl methyl cellulose is a blend of lauric diethanolamide, lauric acid, and polyoxyethylene lauryl ether phosphate.

10. The method in accordance with claim 1, wherein the non-aqueous organic dispersant for the hydroxypropyl methyl cellulose is ethoxylated $C_{12-15}$ alcohol containing 7 moles ethylene oxide per mole.

11. The method according to claim 1, wherein the non-aqueous dispersant for the hydroxypropyl methyl cellulose is stearic acid.

12. The method according to claim 1, wherein the non-aqueous dispersant for the hydroxypropyl methyl cellulose is ethylene glycol distearate.

* * * * *